US010918553B1

(12) United States Patent
Luea et al.

(10) Patent No.: US 10,918,553 B1
(45) Date of Patent: Feb. 16, 2021

(54) MEDICAL TABLE STIRRUP INSERT

(71) Applicant: ComenityMed, LLC, Traverse City, MI (US)

(72) Inventors: Brittany G. Luea, Traverse City, MI (US); Autumn R. Bridger, Meadville, PA (US)

(73) Assignee: ComenityMed, LLC, Traverse City, MI (US)

( * ) Notice: Subject to any disclaimer, the term of this patent is extended or adjusted under 35 U.S.C. 154(b) by 197 days.

(21) Appl. No.: 15/860,946

(22) Filed: Jan. 3, 2018

Related U.S. Application Data

(60) Provisional application No. 62/442,002, filed on Jan. 4, 2017.

(51) Int. Cl.
*A47C 1/00* (2006.01)
*A47C 20/00* (2006.01)
*A47C 20/02* (2006.01)
*A61F 5/00* (2006.01)
*A61G 13/12* (2006.01)

(52) U.S. Cl.
CPC .......... *A61G 13/125* (2013.01); *A47C 20/021* (2013.01)

(58) Field of Classification Search
CPC ........ A47C 20/00; A47C 20/02; A47C 20/021
See application file for complete search history.

(56) References Cited

U.S. PATENT DOCUMENTS

| | | | | | |
|---|---|---|---|---|---|
| 1,945,780 | A * | 2/1934 | Johnson | A43B 21/32 | 36/37 |
| 2,804,363 | A * | 8/1957 | Spielberg | A61G 13/12 | 5/624 |
| 3,309,447 | A * | 3/1967 | Wegley | A43B 7/28 | 264/223 |
| 3,452,978 | A * | 7/1969 | Creelman | A61G 13/12 | 5/624 |
| 3,992,856 | A * | 11/1976 | McGovern | A61G 13/125 | 54/1 |
| 4,046,365 | A * | 9/1977 | Dungan | A61G 13/125 | 5/649 |
| 4,179,826 | A * | 12/1979 | Davidson | A43B 21/32 | 36/129 |
| D263,501 | S * | 3/1982 | Junk | D24/184 | |
| 4,325,380 | A * | 4/1982 | Malkin | A43B 21/32 | 36/140 |

(Continued)

*Primary Examiner* — Peter M. Cuomo
*Assistant Examiner* — Ifeolu A Adeboyejo
(74) *Attorney, Agent, or Firm* — K&L Gates LLP

(57) ABSTRACT

A stirrup insert for covering a stirrup of a medical examination table includes a foot support portion and an engagement portion, which are together a single integral piece of polymeric material, such as silicone or a similar material. The foot support portion has a contoured upper surface configured to receive a patient's foot and a lower surface configured to engage a front surface of a stirrup. The engagement portion extends from a perimeter edge of the foot support portion and curves inward toward the lower surface of the foot support portion to form a curved lip that extends around at least an upper section of the perimeter edge. The engagement portion may be substantially flexible and resilient, so as to be capable of wrapping over an edge of the stirrup and engaging a rear surface of the stirrup, thereby securing the stirrup insert in place relative to the stirrup.

20 Claims, 10 Drawing Sheets

(56) References Cited

U.S. PATENT DOCUMENTS

| | | | | | |
|---|---|---|---|---|---|
| 4,346,525 | A * | 8/1982 | Larsen | A43B 7/144 | 36/145 |
| 4,360,193 | A * | 11/1982 | Mitchell | A61G 13/12 | 5/649 |
| 4,530,173 | A * | 7/1985 | Jesinsky, Jr. | A43B 21/32 | 36/173 |
| 4,928,404 | A * | 5/1990 | Scheuermann | A43B 17/16 | 36/35 R |
| 5,067,256 | A * | 11/1991 | Darby | A43B 7/14 | 36/37 |
| 5,172,494 | A * | 12/1992 | Davidson | A43B 21/26 | 36/173 |
| 5,803,088 | A * | 9/1998 | Blackwell | A61G 13/12 | 128/882 |
| 5,907,877 | A * | 6/1999 | Allgood | A61G 13/10 | 150/154 |
| 6,315,786 | B1 * | 11/2001 | Smuckler | A43B 7/14 | 36/145 |
| 6,629,945 | B1 * | 10/2003 | Stromgren | A61F 13/067 | 602/5 |
| 7,141,032 | B2 * | 11/2006 | Flam | A61F 13/069 | 602/61 |
| 8,296,969 | B2 * | 10/2012 | Granger | A43B 1/0009 | 36/173 |
| 9,072,340 | B2 * | 7/2015 | Huber | A61F 5/0111 | |
| 10,182,615 | B2 * | 1/2019 | Jacobsen | B32B 27/36 | |
| 10,420,669 | B2 * | 9/2019 | Rich | A43B 17/00 | |
| 2009/0199339 | A1 * | 8/2009 | Barr | A61G 13/02 | 5/602 |
| 2012/0184886 | A1 * | 7/2012 | Huber | A47C 20/021 | 602/5 |

* cited by examiner

MEDICAL TABLE STIRRUP INSERT

CROSS REFERENCE TO RELATED APPLICATION

The present application claims priority of U.S. provisional application Ser. No. 62/442,002 filed Jan. 4, 2017, which is hereby incorporated herein by reference in its entirety.

FIELD AND BACKGROUND OF THE INVENTION

The present invention generally relates to foot support devices used with medical tables, beds, chairs, or the like. In particular, the present invention is directed to an insert or cover for a medical table stirrup that supports a patient's foot in a raised or elevated position, such as for use during a medical examination or other medical procedure.

It is common for medical examination tables to provide foot stirrups on the table to support a patient's foot when the patient is seated or laying on the table. Typically, foot stirrups are supported by arms, rods or braces that extend outward from at the end area of the table to locate the patient's foot and thereby position the patient's leg for a medical examination or procedure.

SUMMARY OF THE INVENTION

The present invention provides a stirrup insert for covering the foot receiving portion of a stirrup of a medical examination table, such as to insulate and cushion a patient's foot against a typically rigid metal stirrup that can be uncomfortable and cold to the touch. The stirrup insert may be a single piece of polymer, such as for example a medical grade silicone or another material, that may be easily cleaned and kept sterile. The stirrup insert includes a foot support portion that has a contoured upper surface for receiving a patient's foot and a lower surface that engages the stirrup. The foot support portion is shaped to receive various sized feet and is pliable and compressible to provide a cushion effect between the patient's foot and the stirrup. The stirrup insert also includes an engagement portion that extends rearward from a perimeter edge of the foot support portion and curves inward toward a lower surface of the foot support portion to form a curved lip that engages over upper and outer edges of the stirrup to securely hold the stirrup insert on the stirrup during use.

According to an embodiment of the invention, a stirrup insert for covering a stirrup of a medical examination table includes a foot support portion and an engagement portion, which are together a single integral piece of polymeric material, such as silicone or a similar material. The foot support portion has a contoured upper surface configured to receive a patient's foot and a lower surface configured to engage a front surface of a stirrup. The foot support portion may include a heel section that is formed as a convex lower surface protruding rearward to engage, such as within and/or partially through, the heel opening of a stirrup or rest on a flat or recessed surface of a stirrup that does not have an opening for the heel. The engagement portion extends from a perimeter edge of the foot support portion and curves inward toward the lower surface of the foot support portion to form a curved lip that extends around at least an upper section of the perimeter edge. In a particular embodiment, for example, the engagement portion may extend about the entire perimeter edge and may include a notch at a lower section of the perimeter edge for engaging around the supportive arm or shaft of the stirrup. The engagement portion may be generally elastic whereby it is substantially flexible and resilient, so as to be capable of wrapping over an edge of the stirrup and engaging a rear surface of the stirrup, thereby providing a fixed, elastic tension engagement against the stirrup to detachably secure the stirrup insert in place relative to the stirrup.

The stirrup insert of the present invention is configured for use on variously sized and configured stirrups of differently designed and constructed medical examination tables to provide a comfortable and ergonomic receptacle for a patient's foot. The stirrup insert may be designed as a generally universal size that accommodates multiple varieties of stirrups and exam beds. These and other objects, advantages, purposes and features of this invention will become apparent upon review of the following specification in conjunction with the drawings.

DESCRIPTION OF THE PREFERRED EMBODIMENTS

Figure 1:
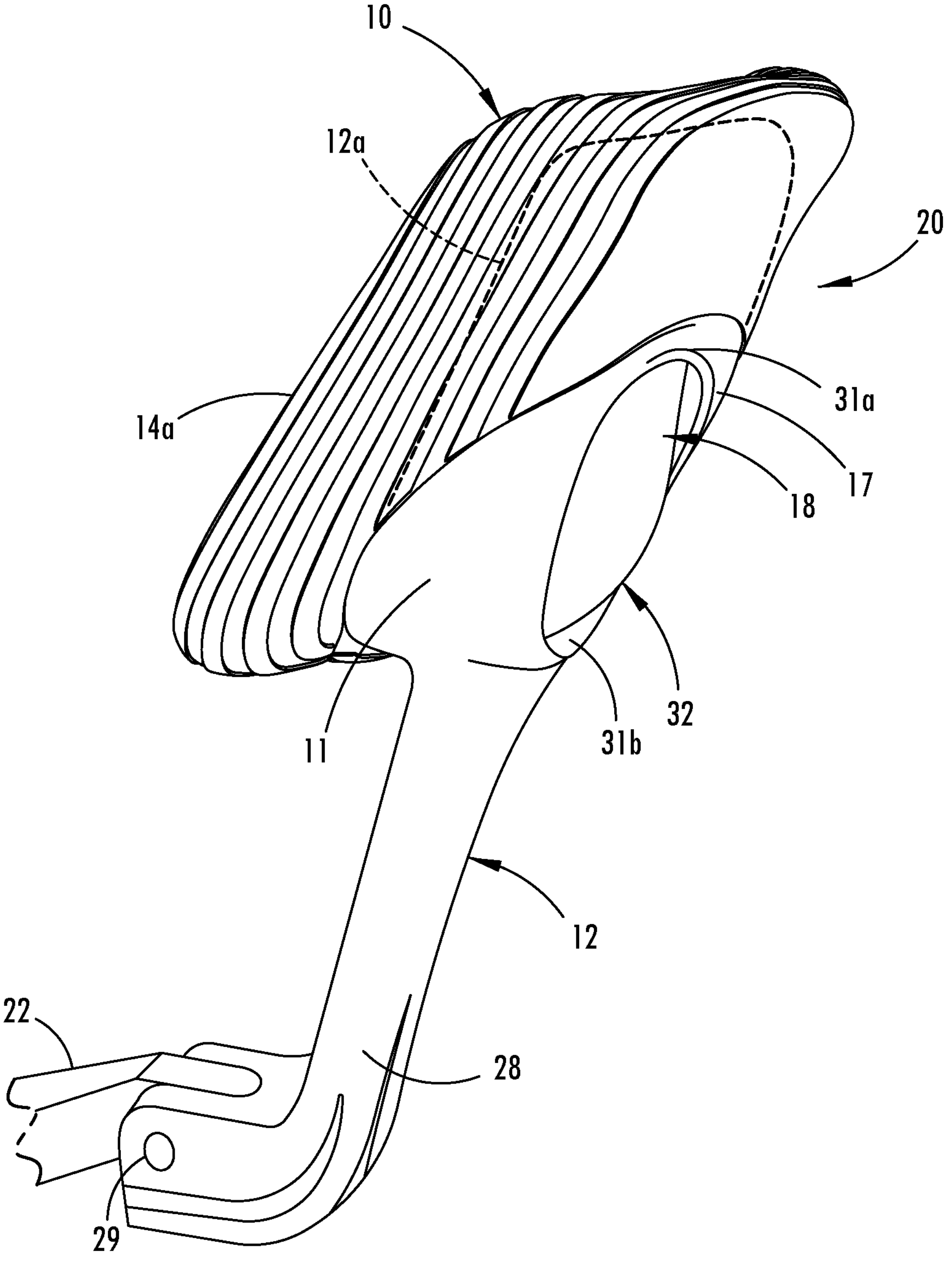
FIG. 1 is a perspective view of a stirrup insert covering a medical table stirrup in accordance with the present invention, where an edge of the stirrup is shown in dashed lines.

Referring now to the drawings and the illustrative embodiments depicted therein, a stirrup cover or stirrup insert 10 is provided for covering the foot receiving portion 11 of a foot support or stirrup 12 (FIGS. 1-4) of a medical examination table, such as to insulate and cushion a patient's foot against a typically rigid metal stirrup that can be cold and otherwise uncomfortable to the touch. Examination table stirrups 12 moreover are typically narrow and, because they are rigid, do not accommodate differently sized feet, thus rendering them further uncomfortable, whereby stirrup insert 10 provides a wider base and surface area for receiving a patient's foot.

In the illustrated embodiment the stirrup insert 10 is a single piece of polymer, such as medical grade or food grade silicone or the like, which can be readily cleaned and kept sterile, such as by means of heat or chemical sterilization. The stirrup insert 10 is configured to be removably attached to the stirrup 12 so it can easily be removed, yet remain securely attached when mounted. The stirrup insert 10 includes a foot support portion 14 that has a contoured upper surface 16 for receiving a patient's foot and a back side 17 with lower surface 18 that engages the stirrup 12. To securely hold the stirrup insert 10 in place on the stirrup 12 during use, the stirrup insert 10 includes a flexible, elastic engagement portion 20 that extends from a perimeter edge 14*a* of the foot support portion 14 and curves rearward and inward toward the lower surface 18 of the foot support portion 14 to form a curved lip that engages over upper and outer edges 12*a* of the stirrup 12. The flexible engagement portion 20 thus comprises a wrap-around edge to engage with the foot receiving portion 11 of stirrup 12, such that the back side portion 17 may be received within an opening of the stirrup 12 or in and additional embodiment of a stirrup without an opening the back side portion may rest on a flat or recessed surface at the heel portion of the stirrup.

Figure 4:
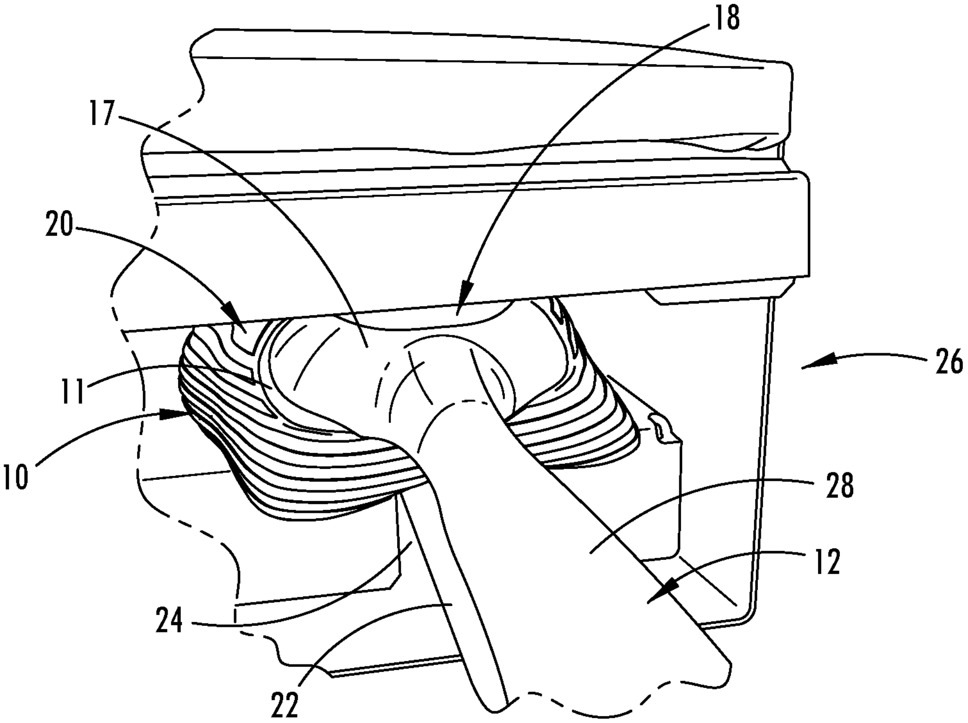
FIG. 4 is a rear perspective view of the covered medical table stirrup in a folded position being retracted into the medical table shown in FIG. 3.

As shown in FIGS. 1-4, the stirrup 12 may be supported by a retractable rod 22 that extends from an opening 24 in table 26. The retractable rod 22 is pivotally attached to a shaft section 28 of the stirrup 12 about a pivot joint 29 that pivots to position the shaft section 28 of the stirrup 12 at an upward extending angle from the retractable rod 22. The shaft section 28 extends to a head section 30 of the stirrup 12, which forms the foot receiving portion 11 and may have an opening 30*a* for receiving a heel of a patient's foot. Again, an additional embodiment of a stirrup may not have an opening at the head section of the stirrup, such that the stirrup may have a flat or recessed surface at the heel portion of the stirrup that would otherwise have the opening. The retractable rod 22 may retract back into the opening 24 in the medical examination table 26 after attaching the stirrup insert 10 over the stirrup 12, such as shown in FIG. 4. Accordingly, the stirrup insert 10 may be sized to be received in the storage opening 24 while remaining engaged with the stirrup 12.

In the embodiment illustrated in FIGS. 1-4, the head section 30 of the stirrup 12 has a loop or perimeter forming opening 30*a*. The back side portion 17 of the stirrup insert 10 includes a heel section 32 (FIG. 6) that has a convex curved and generally wedge shape at the lower surface 18 protruding rearward to engage within and/or partially through the heel opening 30*a* of the stirrup 12. The convex shape of the lower surface 18 at the heel section 32 includes a corner portion or lowermost edge 18*a* (FIG. 9) that separates a lower section 18*b* (FIG. 8) that rests on or engages the lower portion 31*b* of the opening 30*a* and an upper section 18*c* (FIG. 8) that extends upward to contact the front surface of the upper portion 31*a* of the head section 30 of the stirrup 12 (FIG. 1). It is contemplated that the lower surface of the heel section 32 may be alternatively shaped in additional embodiments, such as to substantially match the shape of the heel opening 30*a* and/or include a portion that extends past to snap fit into an opening and/or to include a portion that rests upon an opening or a flat or recessed surface at a heel portion of a stirrup without an opening.

Figure 2:
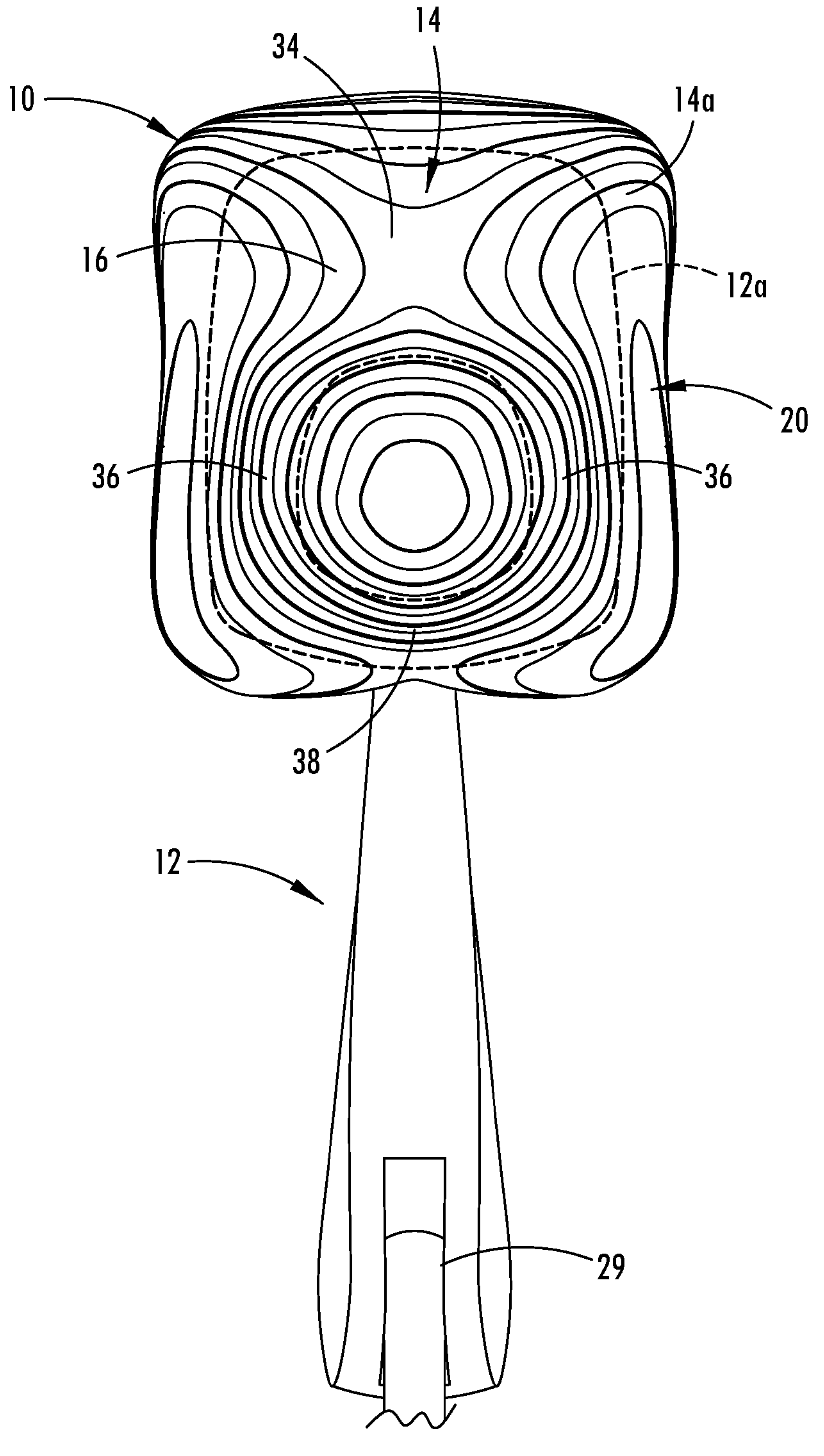
FIG. 2 is a front elevational view of the stirrup insert and covered medical table stirrup shown in FIG. 1, showing the edge of the stirrup in dashed lines.
Figure 3:
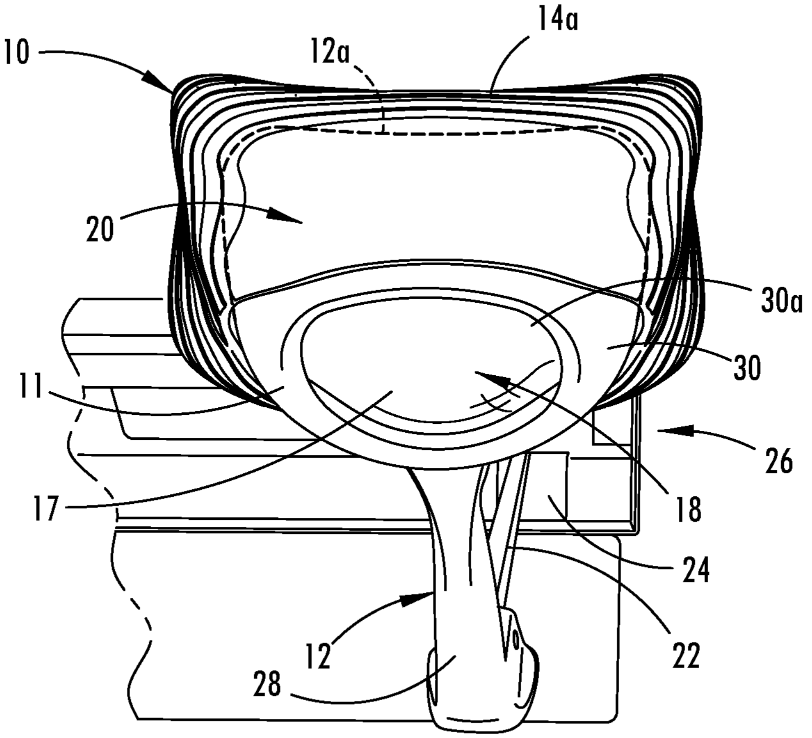
FIG. 3 is a rear perspective view of the stirrup insert and covered medical table stirrup shown in FIG. 1, showing the edge and an opening in the stirrup in dashed lines.
Figure 5:
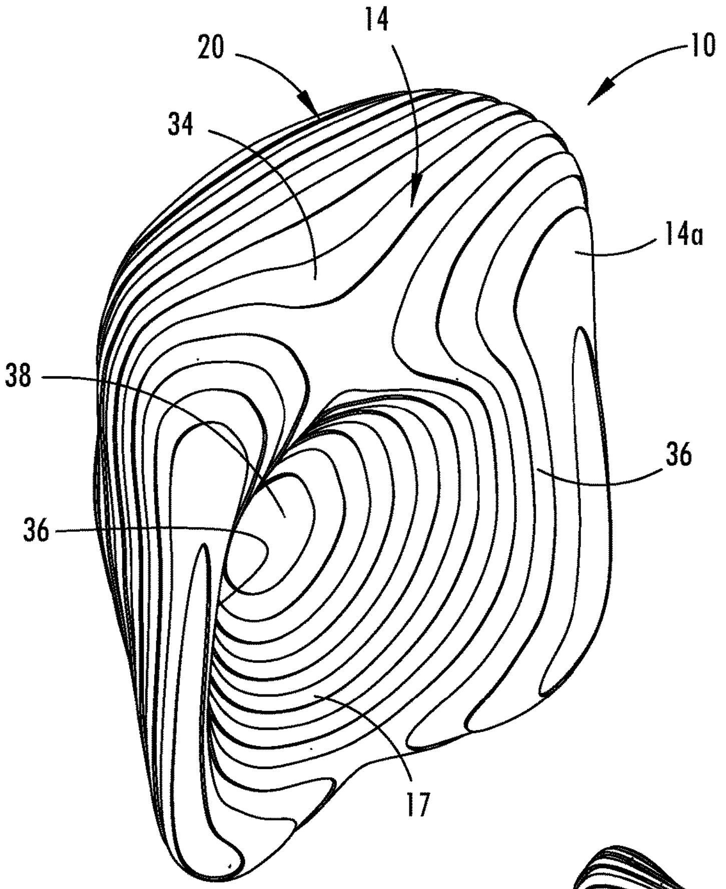
FIG. 5 is a front upper perspective view of the stirrup insert shown in FIG. 1, removed from the medical table stirrup.
Figure 6:
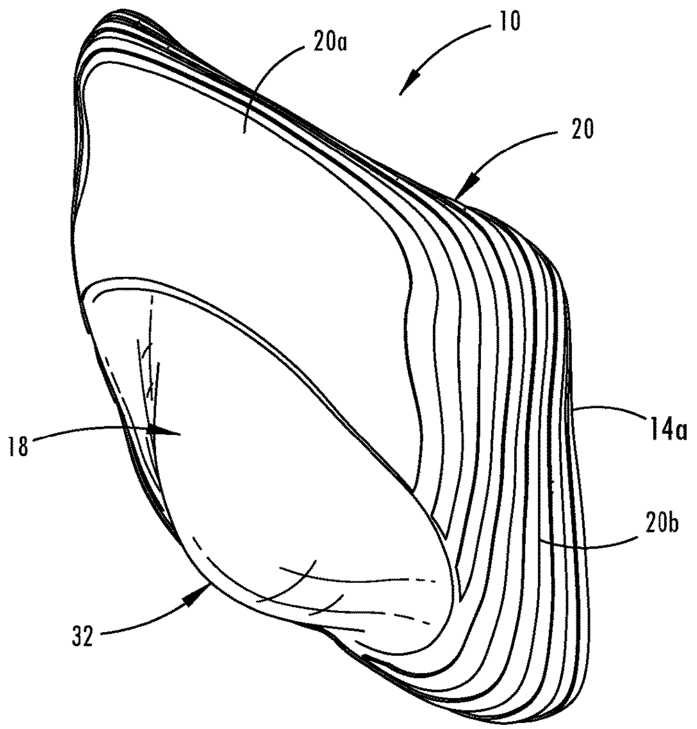
FIG. 6 is an rear upper perspective view of the stirrup insert shown in FIG. 5.
Figure 7:
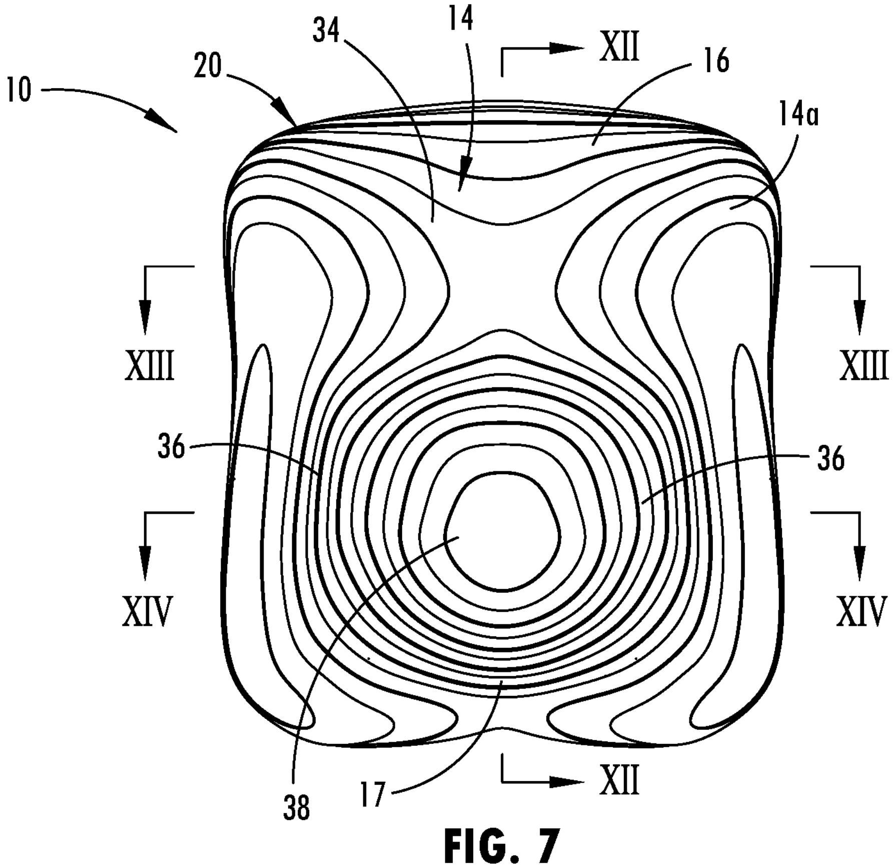
FIG. 7 is a front elevational view of the stirrup insert shown in FIG. 5.

The contoured upper surface 16 of the foot support portion 14 provides a platform or cradle area to receive and support a patient's foot. As shown in FIGS. 2 and 5, the contoured upper surface 16 includes a base surface 34 that is configured to receive a bottom or sole area of the patient's foot. Also, opposing sidewall surfaces 36 extend along lateral sides of the base surface 34 to provide lateral support to the patient's foot. Further, a heel platform surface 38 extends rearward from a lower edge of the base surface 34, also interconnecting with the sidewall surfaces 36 to support the patient's heel and thereby receive the majority of the resting weight of the patient's foot. Accordingly, the foot support portion 14 at the heel platform surface 38 may be generally thicker than the surrounding portions of the stirrup insert 10. The interior convex surfaces of the upper surface 16 are interconnected, without seams, to provide a smooth and continuous interior surface for receiving the patient's foot. The upper surface 16 may also include a non-slip surface formation or texture, such as raised ridges 17 as shown in FIG. 5, so as to provide more friction between the patent's foot and the insert 10. The formation or textures may be provided in various shapes or patterns. As shown in FIGS. 5-7, the ridges 17 encircle the heel platform surface 38 and as the pattern of spaced apart ridges continue away from the central area of the heel platform surface 38 and up the sidewall surfaces 36, they increase in width and span around the outer edges of the upper surface 16 and onto the lower surface 18. It is also conceivable that the contoured upper surface 16 of the foot support portion 14 may be alternatively shaped in additional embodiments to provide an ergonomic supportive surface for a patient's foot.

Figure 12:
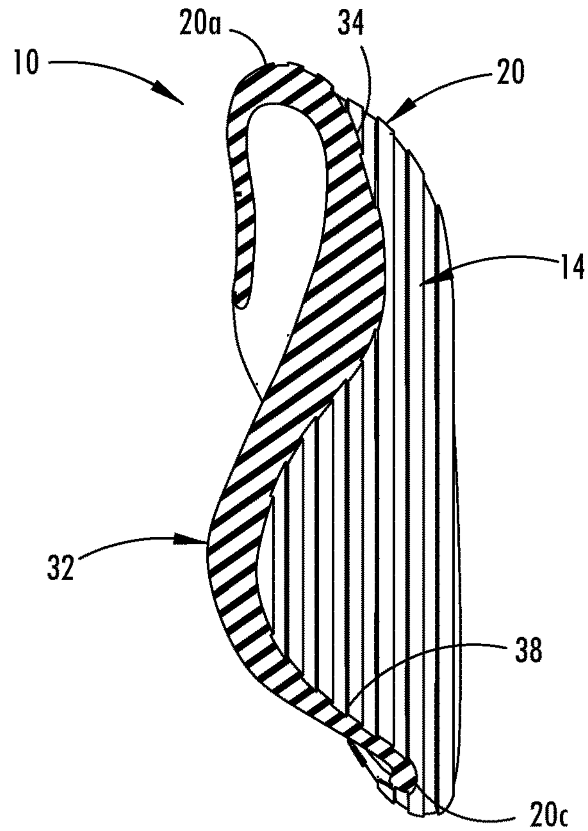
FIG. 12 is a cross-sectional view of the stirrup insert, taken at line XII-XII of FIG. 7.
Figure 13:
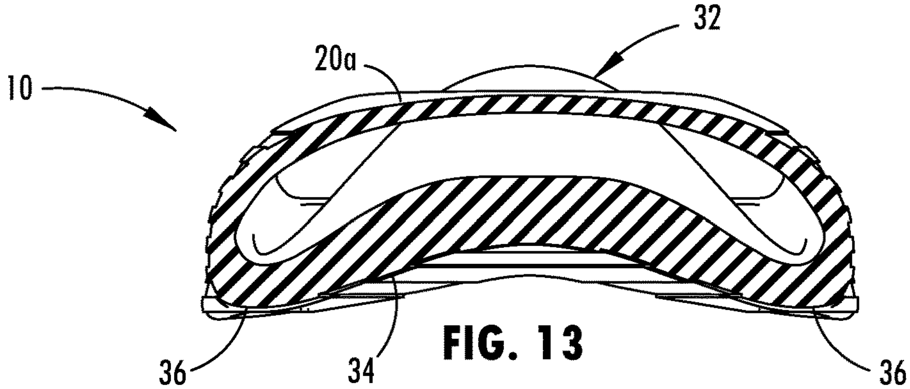
FIG. 13 is a cross-sectional view of the stirrup insert, taken at line XIII-XIII of FIG. 7.
Figure 14:
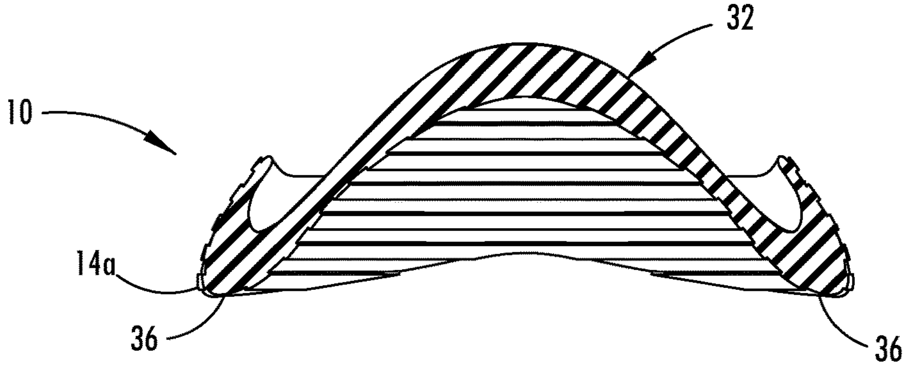
FIG. 14 is a cross-sectional view of the stirrup insert, taken at line XIV-XIV of FIG. 7.

The foot support portion 14 may be pliable to provide a cushioning effect to a patient's foot, yet be sufficiently rigid whereby it maintains its shape even when not mounted to a foot support or stirrup 12. These characteristics may be provided by the thickness of the foot support portion 14, such as shown in FIGS. 12-14 with areas of the foot support portion 14 being sufficiently robust at the areas desired to provide cushioning and slightly thinner at areas that are desired to have more flexibility, such as at the engagement portion 20. Such characteristics may also or alternatively be provided by the material properties of the stirrup insert and/or by the addition of more rigid pieces of material at areas of the stirrup insert that are desired to have such additional rigidity, such as via an insert molding process or the like. It is contemplated that the production version of the stirrup insert 10 will be molded, at least primarily, from a silicone material, such as to provide the exterior surface with the silicone material for cleaning and comfort purposes.

Figure 8:
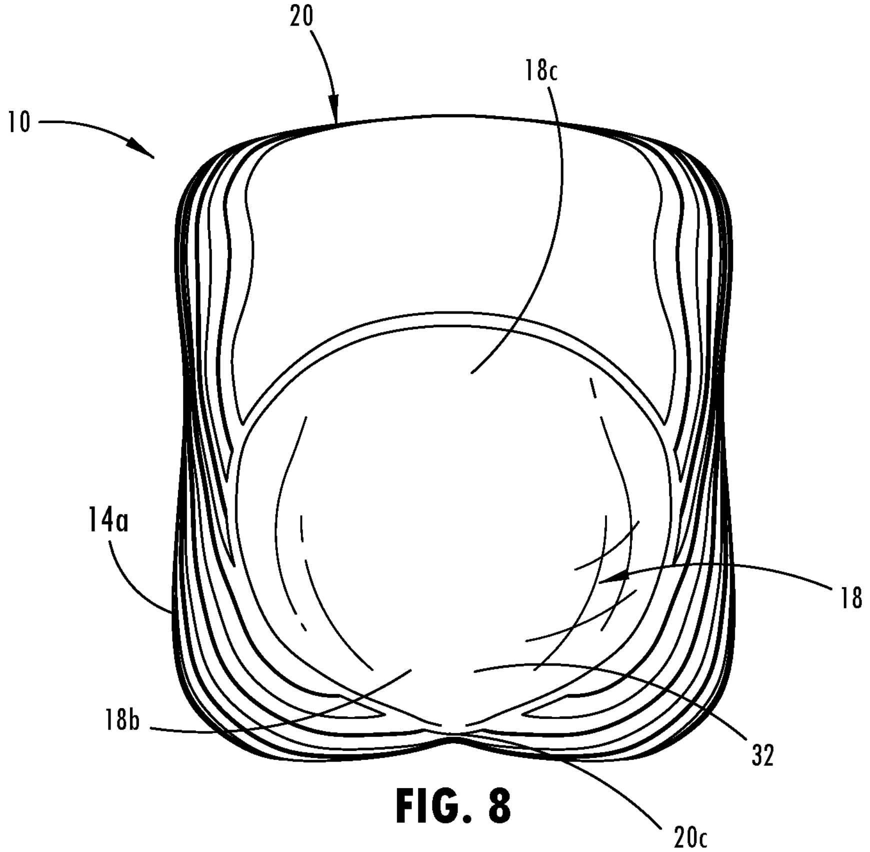
FIG. 8 is a rear elevational view of the stirrup insert shown in FIG. 5.
Figure 9:
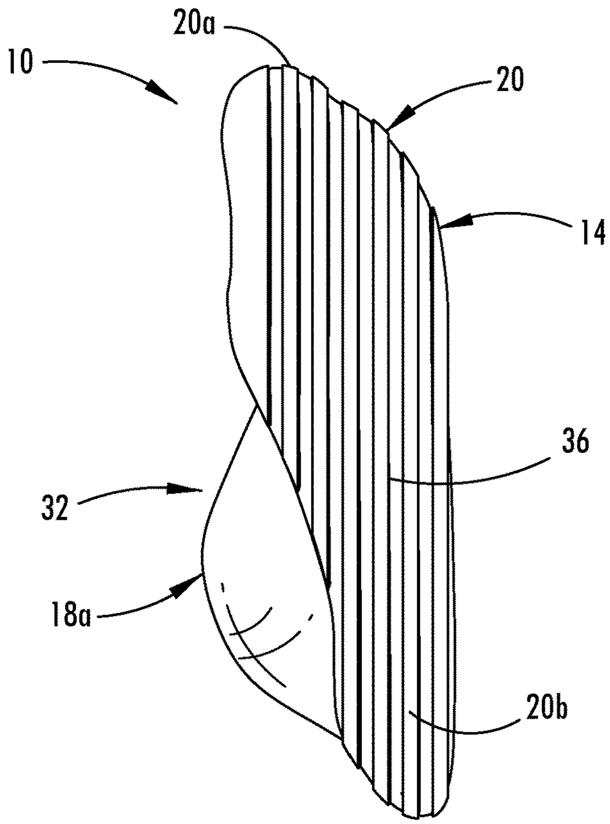
FIG. 9 is a side elevational view of the stirrup insert shown in FIG. 5.
Figure 10:
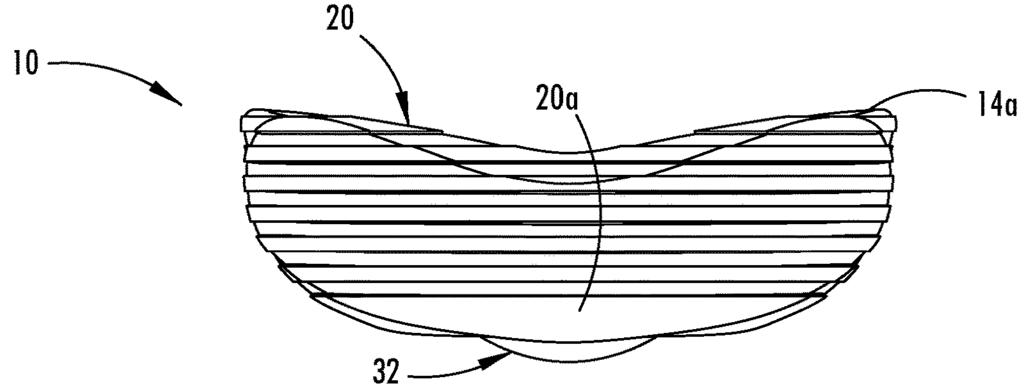
FIG. 10 is an upper elevational view of the stirrup insert shown in FIG. 5.
Figure 11:
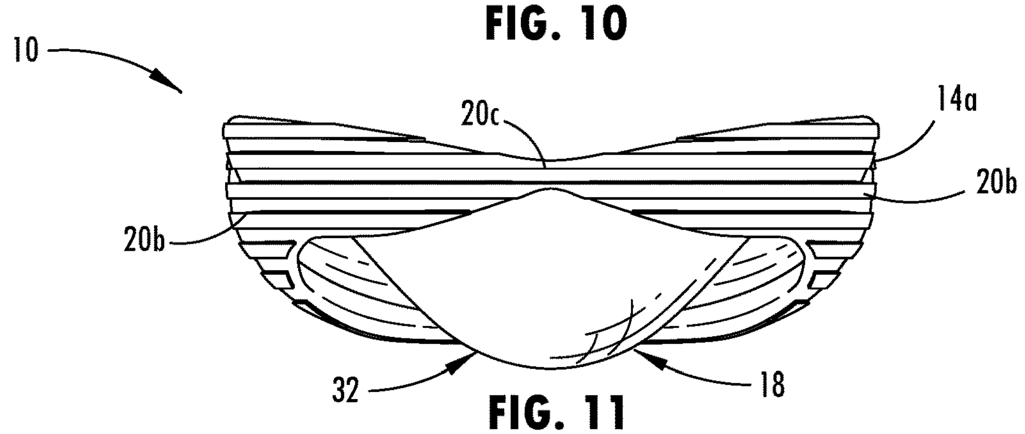
FIG. 11 is a lower elevational view of the stirrup insert shown in FIG. 5.

As shown in FIGS. 6-8, the engagement portion 20 extends rearward from the perimeter edge 14*a* of the foot support portion 14 and curves downward and inward toward the lower surface 18 of the foot support portion 14 to form a curved lip shape or flap at the edge of the stirrup insert 10. The engagement portion 20 has an upper section 20*a* that extends continuously over an upper section of the perimeter edge 14*a* at a length away from the edge 14*a* that tapers as the engagement portion to the lateral section 20*b* that extends downward along the lateral sides of the foot support portion 14 to the lower section of the perimeter edge 14*a*. With reference to FIG. 13, the upper section 20*a* of the engagement portion 20 may, together with the foot support portion 14, wrap laterally around the entire stirrup 12. As shown in FIG. 8, at the lower section of the perimeter edge 14*a*, a lower section 20*c* of the engagement portion 20 has a diminished length that is configured to abut the shaft section 28 of the stirrup 12. The length of the upper and lateral sections 20*a*, 20*b* of the engagement portion 20 thereby extends to engage the rear surface of the stirrup 12 adjacent to a heel opening 30*a*, as shown in FIG. 2. Alternatively, however, a stirrup insert may be configured to have an engagement portion that is configured to extend about the entire perimeter edge of the foot support portion.

The engagement portion 20 of the stirrup insert 10 is substantially flexible and resilient, so as to wrap over the perimeter of the stirrup 12 and elastically engage a rear surface of the stirrup 12, such as to provide an elastic or stretch fit engagement, whereby the stirrup may be elastically stretched and/or snap fit into place over the stirrup. For example, the engagement portion 20 may have a thickness at or near the connection with the foot support portion that is relatively thin to provide an elastic capability. That is, the engagement portion 20 in the illustrated embodiment is unitarily or integrally formed with being integrally molded together. The engagement portion 20 thus provides a thinner portion of material relative to the foot support portion 14 to enable the engagement portion 20 to be wrapped about the perimeter of the head 30. The single integral polymeric piece of the stirrup insert 10 is homogenous, without seams, and comprises a silicone material.

Figure 15:
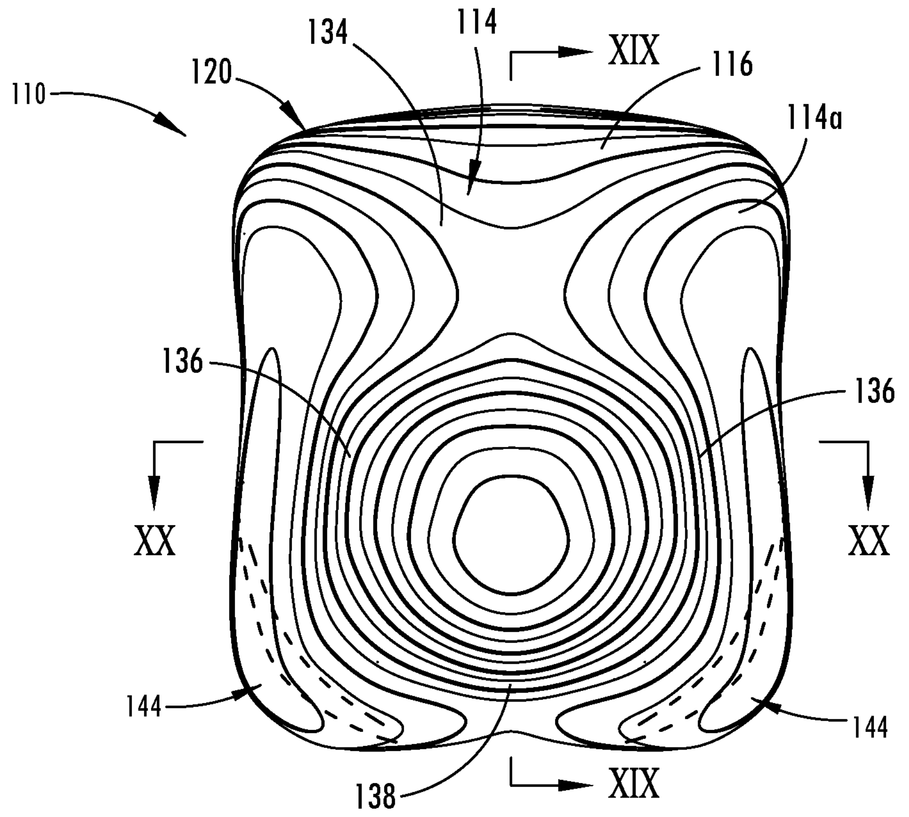
FIG. 15 is a front elevational view of an additional embodiment of a stirrup insert.
Figure 16:
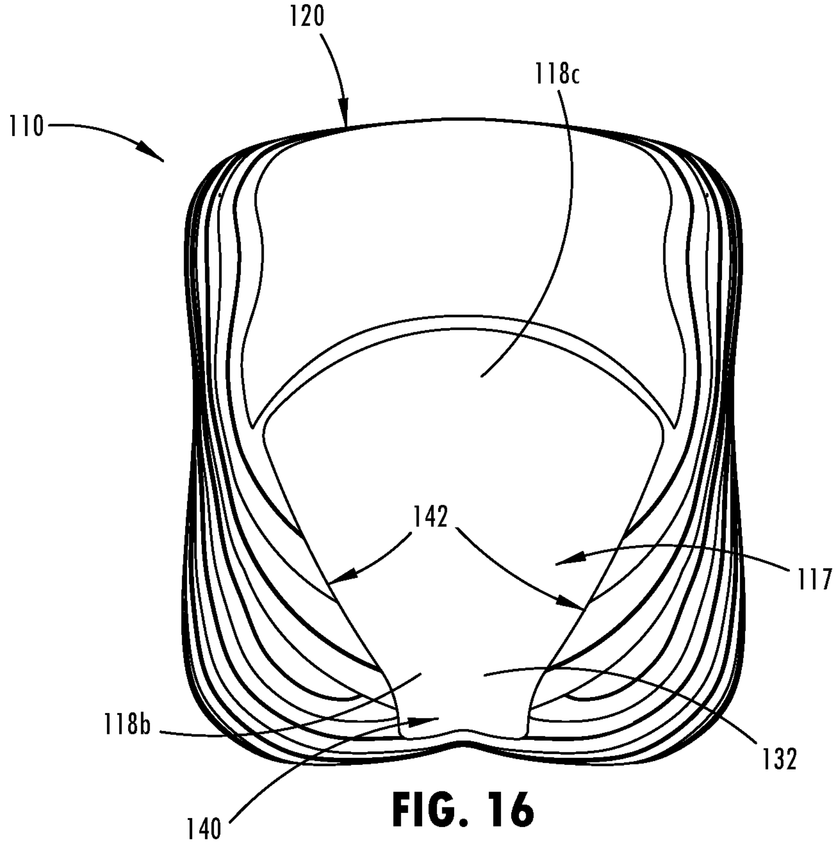
FIG. 16 is a rear elevational view of the stirrup insert shown in FIG. 15.
Figure 17:
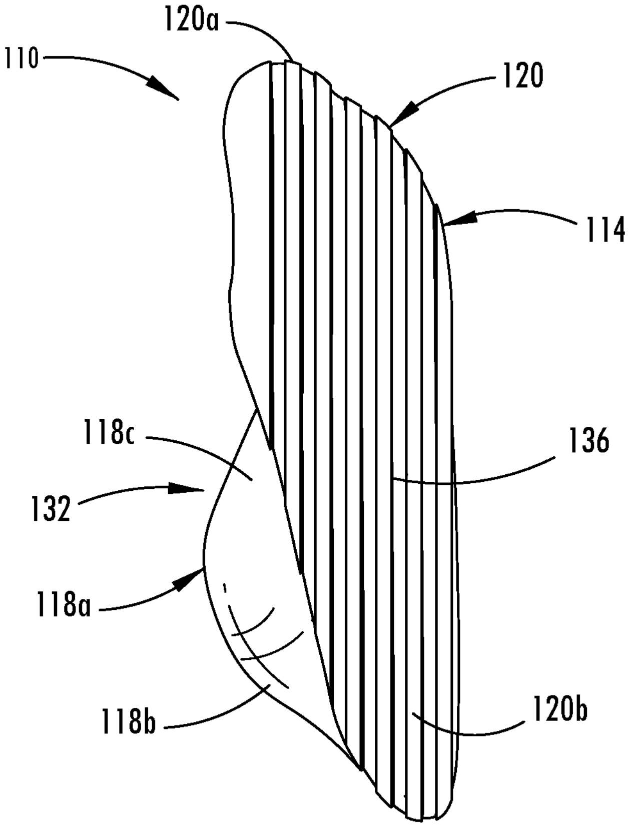
FIG. 17 is a side elevational view of the stirrup insert shown in FIG. 15.

Referring now to FIGS. 15-20, an additional embodiment of the stirrup insert 110 is shown covering a foot support or stirrup of a medical examination table, where this embodiment has slight variations in the shape of the foot support portion 114 and the engagement portion 120 from the stirrup cover or insert 10 illustrated in FIGS. 1-14. The stirrup insert 110 includes a foot support portion 114 that has a contoured upper surface for receiving a patient's foot and a lower surface that engages the stirrup, around the heel opening of the stirrup. The illustrated stirrup insert 110 also includes a flexible, elastic engagement portion 120 that extends from a perimeter edge 114*a* of the foot support portion 114 and curves rearward and inward toward the lower surface 118 of the foot support portion 114 to form a curved lip that engages over upper and outer edges of the stirrup. The flexible engagement portion 120 thus comprises a wrap-around edge to engage with the foot receiving portion of the stirrup, such as with the back side portion 117 being capable of being received within an opening of the stirrup or resting against the heel portion of the stirrup that does not have an opening. The embodiment shown in FIGS. 16 and 18 has a notch or opening 140 at the lower section of the perimeter edge for engaging around the supportive arm or shaft of the stirrup. Thus, the notch or opening 140 allows the lateral sides 142 of the engagement portion 120 to extend further inward and thereby provide a more secure attachment around the stirrup. As shown in FIG. 16, the ridging covering the exterior surface of the stirrup insert may extend onto the back surfaces of the lateral sides 142 of the engagement portion 120.

The back side portion 117 of the stirrup insert 110 includes a heel section 132 (FIG. 16) that has a convex curved and generally wedge shape at the lower surface 118 (FIG. 18) protruding rearward to engage within and/or partially through the heel opening of the stirrup. Alternatively, the heel section 132 of the back side portion 117 may simply rest on or interface with a surface of the heel portion of a stirrup that does not have an opening at the heel. The depth that the illustrated heel section 132 protrudes downward or rearward past the edge of the lateral sections 120*b* of the engagement portion 120 is generally less than the other illustrated embodiment, such as is evident when comparing FIGS. 11 and 18. The convex shape of the lower surface 118 at the heel section 132 still includes a corner portion or lowermost edge 18*a* (FIG. 17) that separates a lower section 118*b* that rests on or engages the lower portion of the stirrup opening and an upper section 118*c* that extends upward to contact the front surface of the upper portion of the head section of the stirrup, such as shown in FIG. 1.

Figure 18:
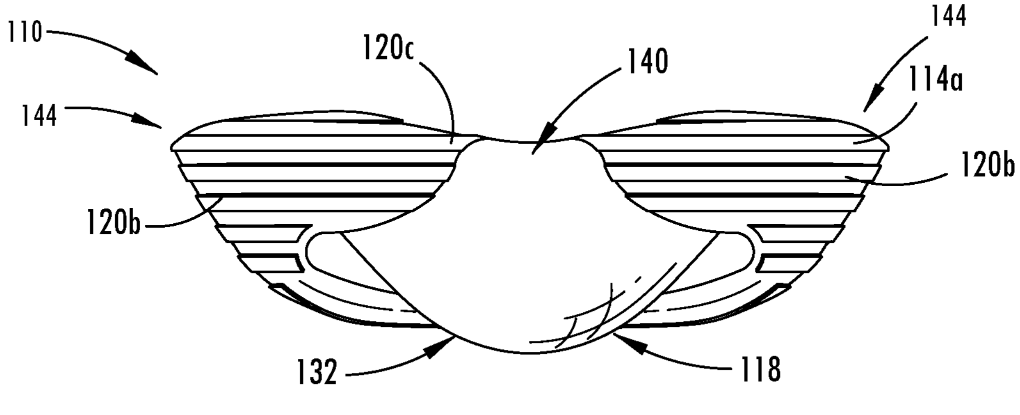
FIG. 18 is a lower elevational view of the stirrup insert shown in FIG. 15.
Figure 19:
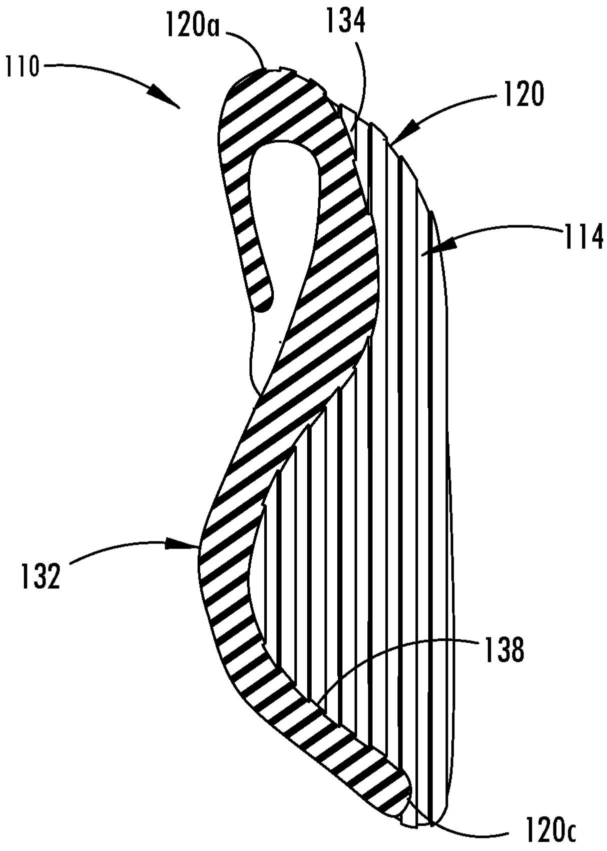
FIG. 19 is a cross-sectional view of the stirrup insert, taken at line XIX-XIX of FIGS. 15.
Figure 20:
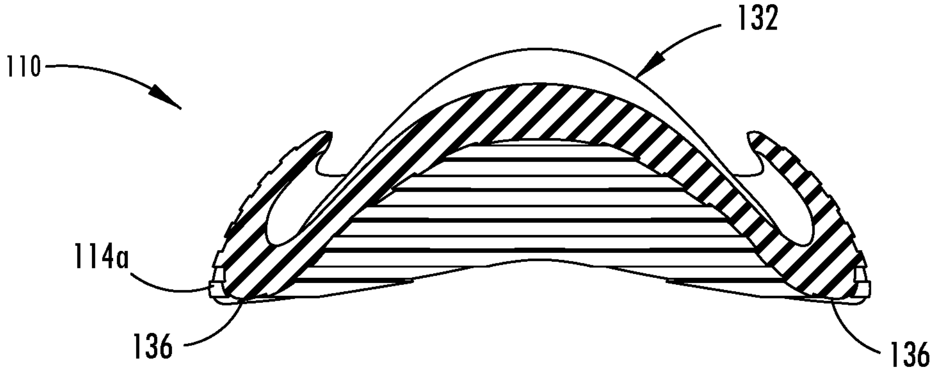
FIG. 20 is a cross-sectional view of the stirrup insert, taken at line XX-XX of FIG. 15.

The contoured upper surface 116 of the foot support portion 114 provides a platform or cradle area to receive and support a patient's foot. As shown in FIG. 15, the contoured upper surface 116 includes a base surface 134 that is configured to receive a bottom or sole area of the patient's foot. Also, opposing sidewall surfaces 136 extend along lateral sides of the base surface 134 to provide lateral support to the patient's foot. Further, a heel platform surface 138 extends rearward from a lower edge of the base surface 134, also interconnecting with the sidewall surfaces 136 to support the patient's heel and thereby receive the majority of the resting weight of the patient's foot. As also shown in FIGS. 15 and 18, the lower corners 144 are curved back further than the embodiment shown in the embodiment illustrated in FIGS. 1-14. By curving the corners 114 back, the stirrup insert 112 is capable of being received in smaller storage openings generally without catching or contacting the table.

Again, the foot support portion 114 may be pliable to provide a cushioning effect to a patient's foot, yet be sufficiently rigid whereby it maintains its shape even when not mounted to a stirrup. The embodiment illustrated in FIG. 19 has an increased thickness at the upper and lower edges of the engagement portion 120, such as evident when comparing FIGS. 12 and 19. This increased thickness adds robust and stiffness to these edge areas.

The stirrup insert of the present invention may be readily cleaned, such as by wiping with chemicals while mounted to an examination table between patients, or may be removed and cleaned in a dishwasher or the like. Changes and modifications in the specifically described embodiments can be carried out without departing from the principles of the present invention which is intended to be limited only by the scope of the appended claims, as interpreted according to the principles of patent law including the doctrine of equivalents.

The invention claimed is:

1. A stirrup insert for covering a stirrup of a medical examination table, wherein perimeter edges of the stirrup includes an upper edge and outer edges of the stirrup, said stirrup insert comprising:

a foot support portion having a contoured upper surface configured to receive a patient's foot and a lower surface opposite the contoured upper surface configured to engage a front surface of a stirrup, wherein the foot support portion includes a heel section that comprises a concave upper surface and a convex lower surface and is configured to receive a patient's heel;

an engagement portion extending from a perimeter edge of the foot support portion and curving toward the lower surface of the foot support portion to form a curved lip, wherein the curved lip includes an upper section and lateral sections that extend inwardly for receiving the stirrup;

wherein the upper section and the lateral sections of the engagement portion are substantially flexible and configured to wrap over the upper edge and the outer edges, respectively, of the stirrup when engaged therewith;

wherein the engagement portion defines an insert opening providing access into the curved lip for receiving the stirrup and exposing and surrounding the convex lower surface of the heel section such that a portion of the convex lower surface of the heel section partially protrudes through the insert opening; and wherein the foot support portion and the engagement portion comprise a single integral flexible polymeric piece.

2. The stirrup insert of claim 1, wherein the heel section is configured to protrude rearward and both engage the stirrup and extend through a heel opening of the stirrup when the stirrup insert is engaged with the stirrup.

3. The stirrup insert of claim 2, wherein the heel section protrudes rearward a distance that is configured to extend partially through a heel opening of the stirrup.

4. The stirrup insert of claim 2, wherein the heel section includes a rear surface that is configured to rest against a support surface that extends across a heel portion of the stirrup.

5. The stirrup insert of claim 1, wherein the engagement portion is substantially resilient to stretch into engagement over the upper and outer edges of the stirrup.

6. The stirrup insert of claim 1, wherein the single integral polymeric piece comprises a silicone material.

7. The stirrup insert of claim 1, wherein the curved lip of the engagement portion extends from lateral sides of the foot support portion and is configured to engage the rear surface of the stirrup adjacent to a heel opening of the stirrup.

8. The stirrup insert of claim 1, wherein a lower section of the perimeter edge includes an opening that is configured to engage around an arm that supports the stirrup.

9. The stirrup insert of claim 1, wherein the contoured upper surface of the foot support portion comprises (i) a base surface configured to receive a bottom of the patient's foot, (ii) opposing sidewall surfaces extending from lateral sides of the base surface, and (iii) a heel support surface extending from a lower side of the base surface.

10. The stirrup insert of claim 1, wherein the contoured upper surface of the foot support portion comprises an anti-slip texture that has a ridges.

11. A stirrup insert for covering a stirrup of a medical examination table, said stirrup insert comprising:

a foot support portion having a contoured upper surface configured to receive a patient's foot and a lower surface configured to engage a front surface of a stirrup, wherein the foot support portion includes a heel section that comprises a concave upper surface and a convex lower surface;

an engagement portion extending rearward from at least a section of a perimeter edge of the foot support portion and curving inward to form a curved lip configured to engage over a corresponding edge of the stirrup, wherein the curved lip of the engagement portion comprises an opening for engaging around an arm that supports the stirrup, and wherein the engagement portion is substantially resilient to stretch fit over the remaining perimeter of the edge of the stirrup when engaged with the stirrup;

wherein at least a portion of the convex lower surface of the heel section extends rearward past the engagement portion with the engagement portion at least partially surrounding the convex lower surface; and wherein the foot support portion and the engagement portion comprise a single integral flexible polymeric piece.

12. The stirrup insert of claim 11, wherein the engagement portion is substantially flexible and configured to wrap over the edge of the stirrup to engage a rear surface of the stirrup.

13. The stirrup insert of claim 11, wherein the heel section protrudes rearward and engages within and partially through a heel opening of the stirrup.

14. The stirrup insert of claim 11, wherein the foot support portion includes a heel section that comprises a concave upper surface and a lower surface that is configured to rest against a support surface that extends across a heel portion of the stirrup.

15. The stirrup insert of claim 11, wherein the single integral polymeric piece comprises a silicone material.

16. The stirrup insert of claim 11, wherein the engagement portion extends from lateral sides of the foot support portion.

17. The stirrup insert of claim 11, wherein the engagement portion extends rearward from an upper section and lateral side portions of the perimeter edge of the foot support portion.

18. The stirrup insert of any of claims 11, wherein the contoured upper surface of the foot support portion comprises an anti-slip texture that has a ridges.

19. A method of covering a stirrup of a medical examination table, said method comprising:

engaging a lower surface of a foot support portion of a stirrup insert with a front surface of the stirrup, wherein the foot support portion includes a heel section configured to receive a patient's foot, wherein the heel section comprises a concave upper surface and a convex lower surface;

elastically stretching an upper section and lateral sections of an engagement portion of the stirrup insert over an upper edge and outer edges of the stirrup to secure the stirrup insert in place relative to the stirrup with the convex lower surface extending into an opening of the stirrup; and wherein the engagement portion extends rearward from a perimeter edge of the foot support portion and curves inward toward the lower surface of the foot support portion to form a curved lip that extends around the perimeter edge of the foot support portion, and wherein the engagement portion is configured to elastically stretch into engagement with the perimeter edge of the stirrup.

20. The method of claim 19, wherein upon retracting the stirrup into a storage opening of the medical examination table, the stirrup insert is sized to be received in the storage opening while remaining engaged with the stirrup.

* * * * *